US010322866B2

(12) United States Patent
Bramwell

(10) Patent No.: US 10,322,866 B2
(45) Date of Patent: Jun. 18, 2019

(54) THERMALLY INSULATED LIVESTOCK MEDICATION CONTAINER

(71) Applicant: Darla Bramwell, Chromo, CO (US)

(72) Inventor: Darla Bramwell, Chromo, CO (US)

( * ) Notice: Subject to any disclaimer, the term of this patent is extended or adjusted under 35 U.S.C. 154(b) by 0 days.

(21) Appl. No.: 15/642,532

(22) Filed: Jul. 6, 2017

(65) Prior Publication Data

US 2018/0194533 A1 Jul. 12, 2018

Related U.S. Application Data

(63) Continuation-in-part of application No. 29/599,965, filed on Apr. 7, 2017, now Pat. No. Des. 821,665.

(60) Provisional application No. 62/445,369, filed on Jan. 12, 2017.

(51) Int. Cl.

| | |
|---|---|
| ***B65D 81/38*** | (2006.01) |
| ***A61J 1/00*** | (2006.01) |
| ***A61D 7/00*** | (2006.01) |
| ***A61J 1/16*** | (2006.01) |
| *A61K 9/00* | (2006.01) |

(52) U.S. Cl.

CPC ........... *B65D 81/3813* (2013.01); *A61D 7/00* (2013.01); *A61J 1/00* (2013.01); *A61J 1/165* (2013.01); *B65D 81/3825* (2013.01); *A61K 9/0019* (2013.01)

(58) Field of Classification Search

CPC .... A45C 11/20; A45C 2013/026; A47J 41/00; B67D 5/62; B67D 1/08; B67D 1/16; B67D 1/04; B65D 1/0857; F25D 2400/10; F25D 2331/8014; F25D 2303/0821; Y10S 62/13

USPC ...... 206/364, 828; 220/592.03, 915.2, 915.1, 220/592.28, 592.09; 62/457.2, 457.1, 62/457.9, 457.7

See application file for complete search history.

(56) References Cited

U.S. PATENT DOCUMENTS 5,505,307 A * 4/1996 Shink .................... B60N 3/103 206/541
6,467,299 B1 10/2002 Coetzee
8,256,242 B1 * 9/2012 Evans ................. A45C 13/262 62/457.7

(Continued)

FOREIGN PATENT DOCUMENTS

CN 203767295 U 8/2014

OTHER PUBLICATIONS

Office Action issued by the Canadian Intellectual Property Office for Application Serial No. 2,988,719; dated Nov. 29, 2018.

*Primary Examiner* — J. Gregory Pickett
*Assistant Examiner* — Tia Cox
(74) *Attorney, Agent, or Firm* — Dunlap Bennett & Ludwig PLLC; Brendan E. Squire

(57) ABSTRACT

A livestock medication containment and administration container has a thermally insulated body defining an interior cavity and a top opening. A lid is movably attached to the thermally insulated body and has one or more apertures extending through the lid that are configured to receive a dispensing end of a livestock medication delivery device. Divider panels provide interior compartments for storage of livestock medication vials and associated administration supplies. Preferably, the lid is divided so that access to the medication and administration supplies may be accomplished through a first lid side while the medication delivery devices are carried in a second lid side.

18 Claims, 10 Drawing Sheets

25
18
28
26
16
22
24
29
12
12

(56) References Cited

U.S. PATENT DOCUMENTS

| | | | | |
|---|---|---|---|---|
| 2013/0043285 | A1* | 2/2013 | Cordray ................ | A45C 11/20 224/148.3 |
| 2014/0190201 | A1 | 7/2014 | El-Rahim | |

* cited by examiner

THERMALLY INSULATED LIVESTOCK MEDICATION CONTAINER

CROSS-REFERENCE TO RELATED APPLICATION

This application claims the benefit of priority of U.S. provisional application No. 62/445,369, filed Jan. 12, 2017 the contents of which are herein incorporated by reference. This application is a continuation in part of U.S. design patent application number 29/599,965, filed Apr. 7, 2017, the contents of which are herein incorporated by reference.

BACKGROUND OF THE INVENTION

The present invention relates to thermally insulated containers and, more particularly, thermally insulated containers for carrying and dispensing medications for livestock.

In managing a herd of livestock, such as cows, goats, pigs, chickens, and the like, it is often necessary to administer medications to the livestock for prophylactic purposes or in response to a disease condition exhibited by the animals. These medications typically must be maintained within a temperature controlled environment to prevent spoilage of the medication or to ensure that the medication may be delivered to the livestock.

The medications are typically administered by a medication delivery device. However, presently in the art, there is no way of conveniently storing the medication delivery device while not actively administering the medication to the livestock. Similarly, once the medication delivery device has been charged with a medication, there is no way to maintain the medication within the delivery device in a thermally protected environment.

As can be seen, there is a need for an improved thermally insulated livestock medication container.

SUMMARY OF THE INVENTION

In one aspect of the present invention, a livestock medication container, includes a thermally insulated body having a plurality of upstanding sidewalls, a bottom wall interconnecting the plurality of upstanding sidewalls to define an interior cavity, and a top opening. A top lid movably attached to at least one of the plurality of upstanding sidewalls. The top lid is configured to close the top opening in a closed position. One or more apertures extend through the top lid and are configured to receive a dispensing end of a livestock medication dispenser. One or more dividers are removably received within the interior cavity, to define a plurality of interior compartments. The top lid may divided between a first lid portion covering a first portion of the top opening and a second lid portion covering a second portion of the top opening. The first lid portion covers at least one of the plurality of interior compartments, while the second lid portion covers at least another of the plurality of interior compartments.

A first flange extends from an interior edge the first lid portion and a second flange extends from an interior edge of the second lid portion. The first flange and the second flange cooperatively engage one another to seal the top opening across a transverse aspect of the thermally insulated body. Preferably, the first flange overlies the second flange to prevent opening of the second lid portion without opening the first lid portion.

In a preferred embodiment, the apertures are defined in the second lid portion. A containment bin may be carried within the interior cavity and positioned beneath the one or more apertures.

At least one of the plurality of interior compartments is configured to receive a livestock medication vial. At least one of the plurality of interior compartments is configured to receive a thermally active package, which may be a cold pack, or a heat pack.

These and other features, aspects and advantages of the present invention will become better understood with reference to the following drawings, description and claims.

DETAILED DESCRIPTION OF THE INVENTION

Figure 1:
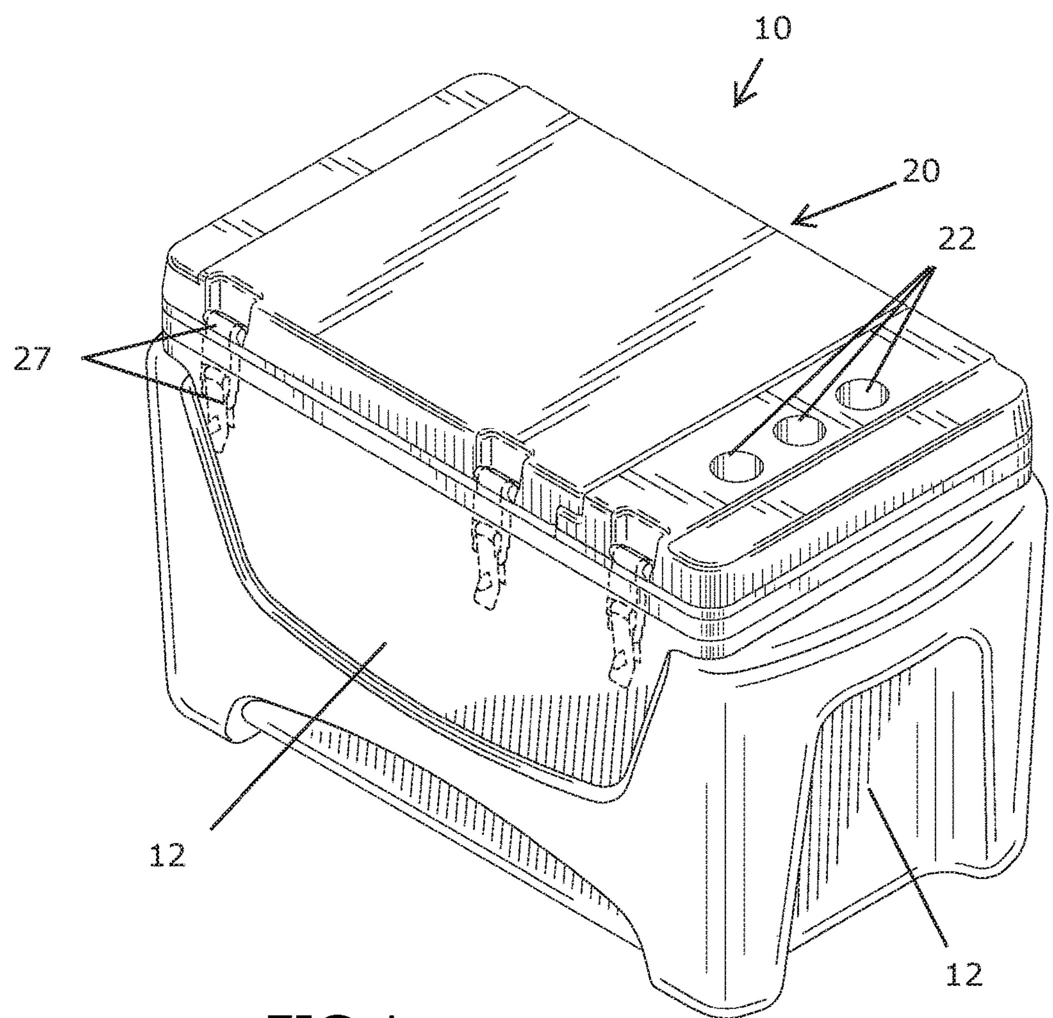
FIG. 1 is a top front perspective view of an embodiment of a livestock vaccination cooler.
Figure 2:
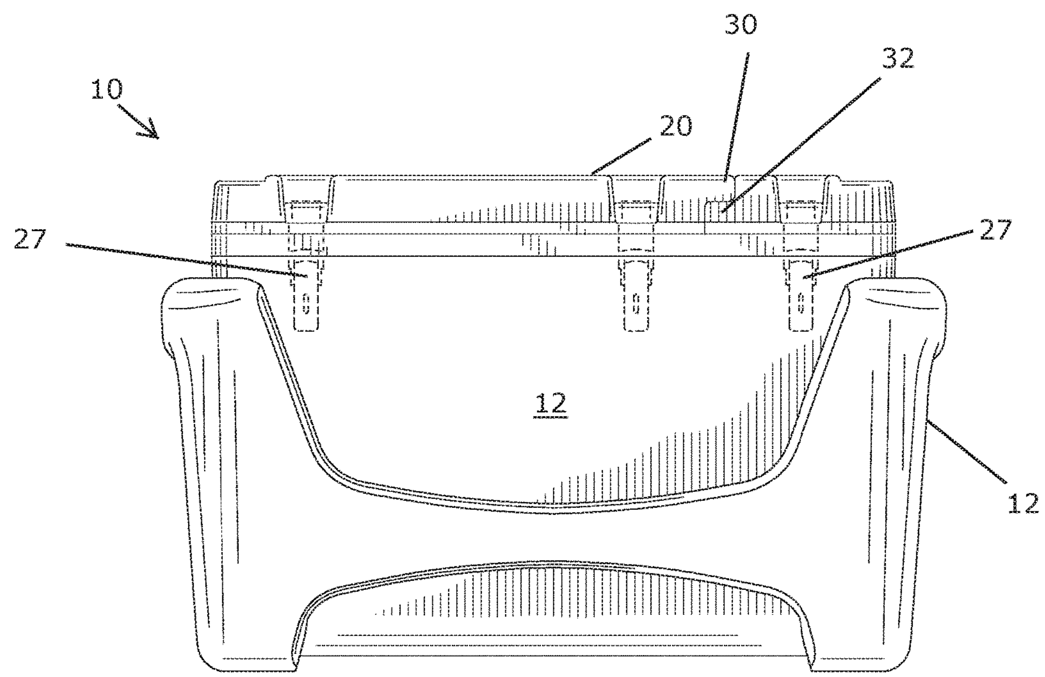
FIG. 2 is a front elevation view of the livestock vaccination cooler.
Figure 3:
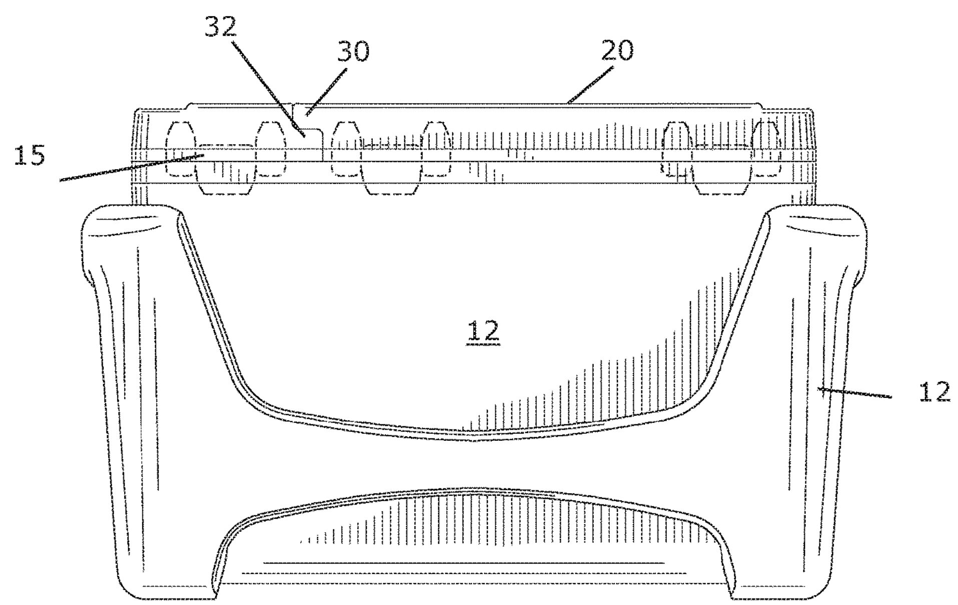
FIG. 3 is a rear elevation view of the livestock vaccination cooler.
Figure 4:
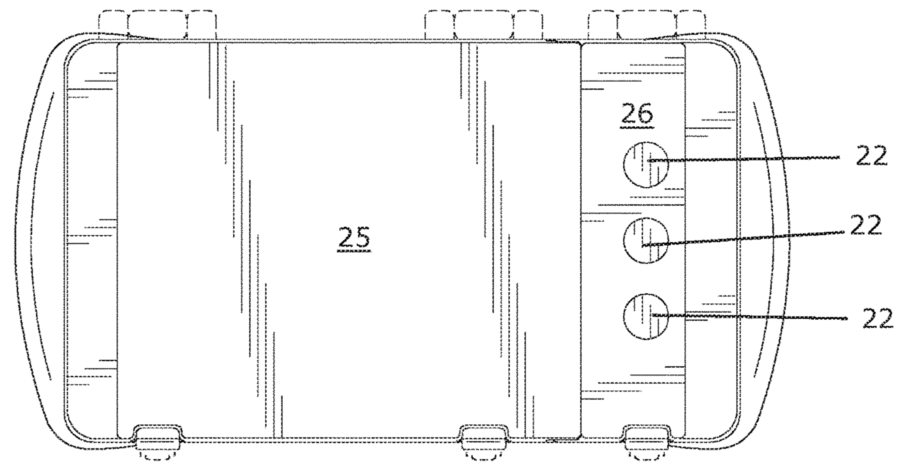
FIG. 4 is a top plan view of the livestock vaccination cooler.
Figure 5:
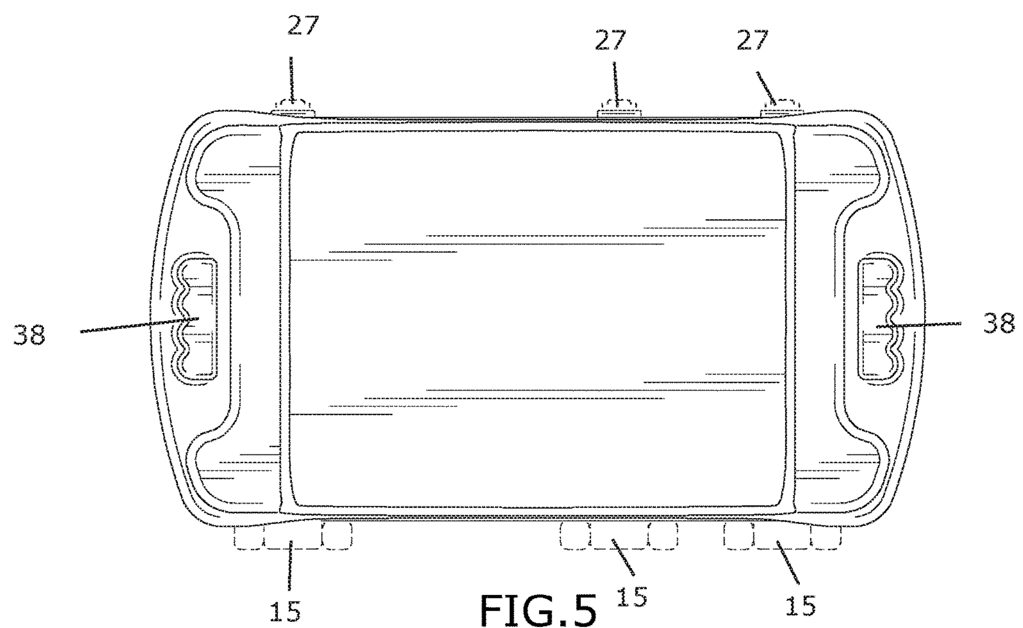
FIG. 5 is a bottom plan view of the livestock vaccination cooler.
Figure 6:
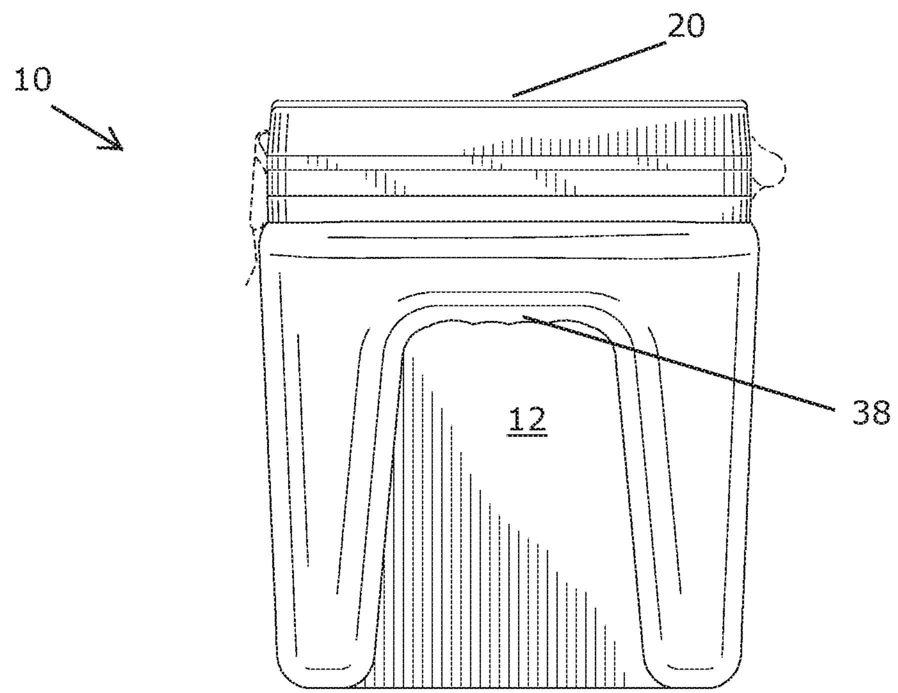
FIG. 6 is a right side elevation view of the livestock vaccination cooler.
Figure 7:
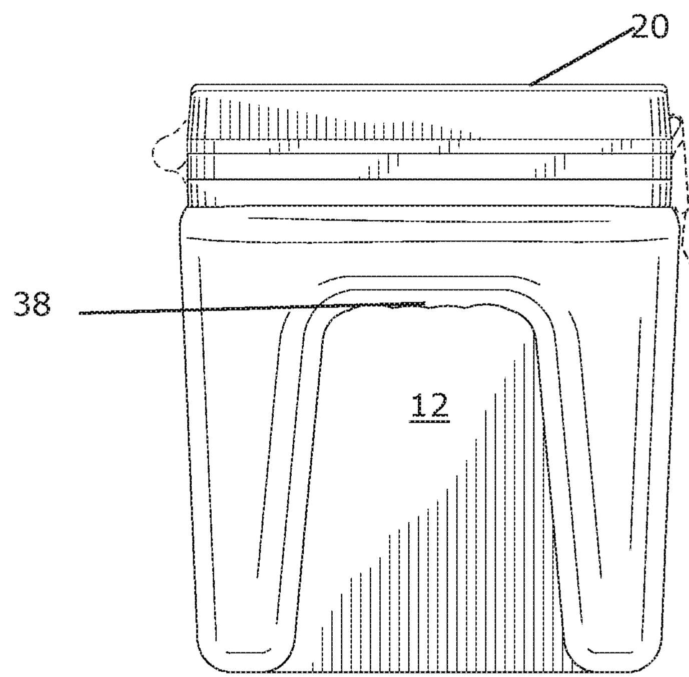
FIG. 7 is a left side elevation view of the livestock vaccination cooler.
Figure 8:
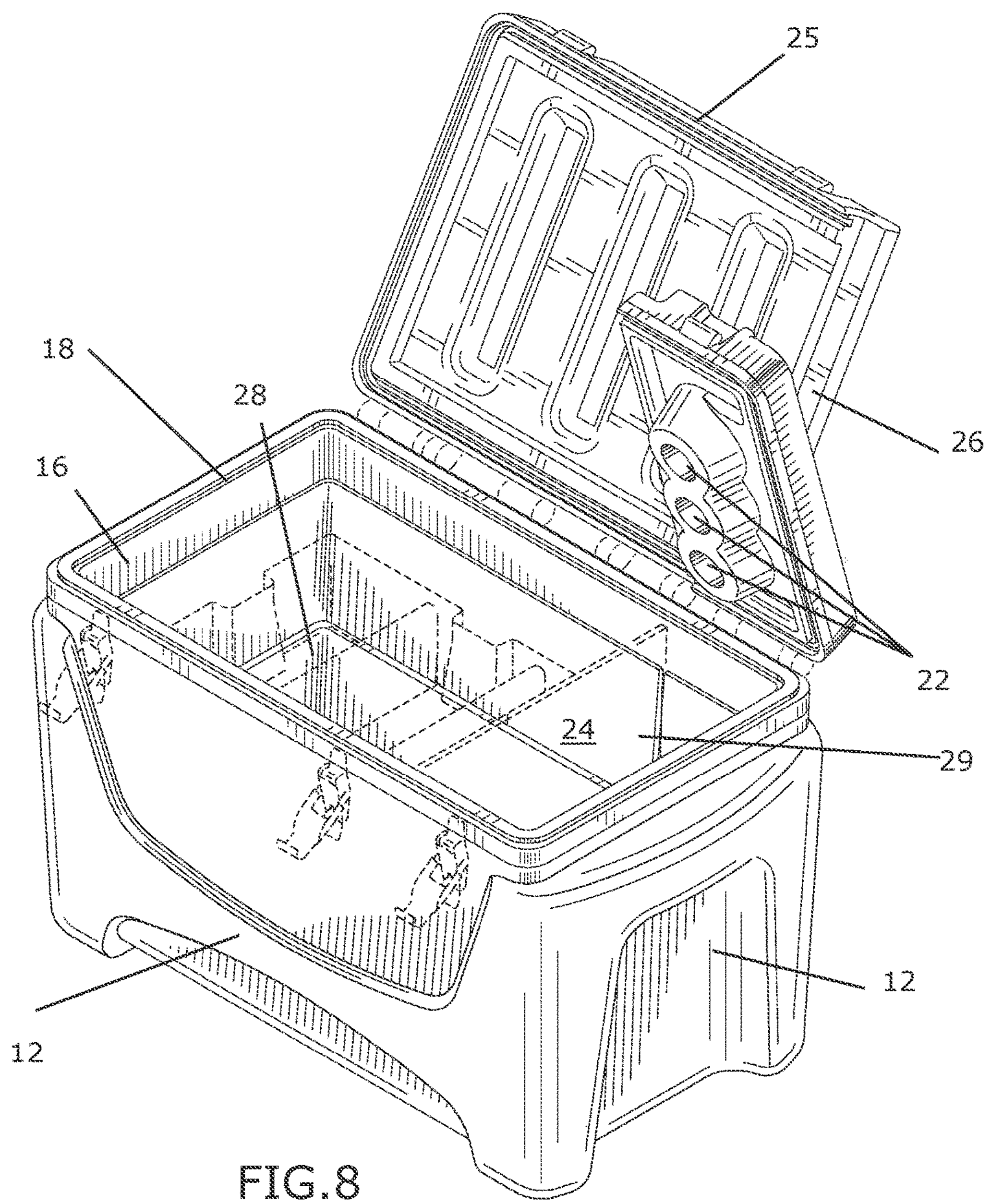
FIG. 8 is a top front perspective view of the livestock vaccination cooler, shown with both lids open.
Figure 9:
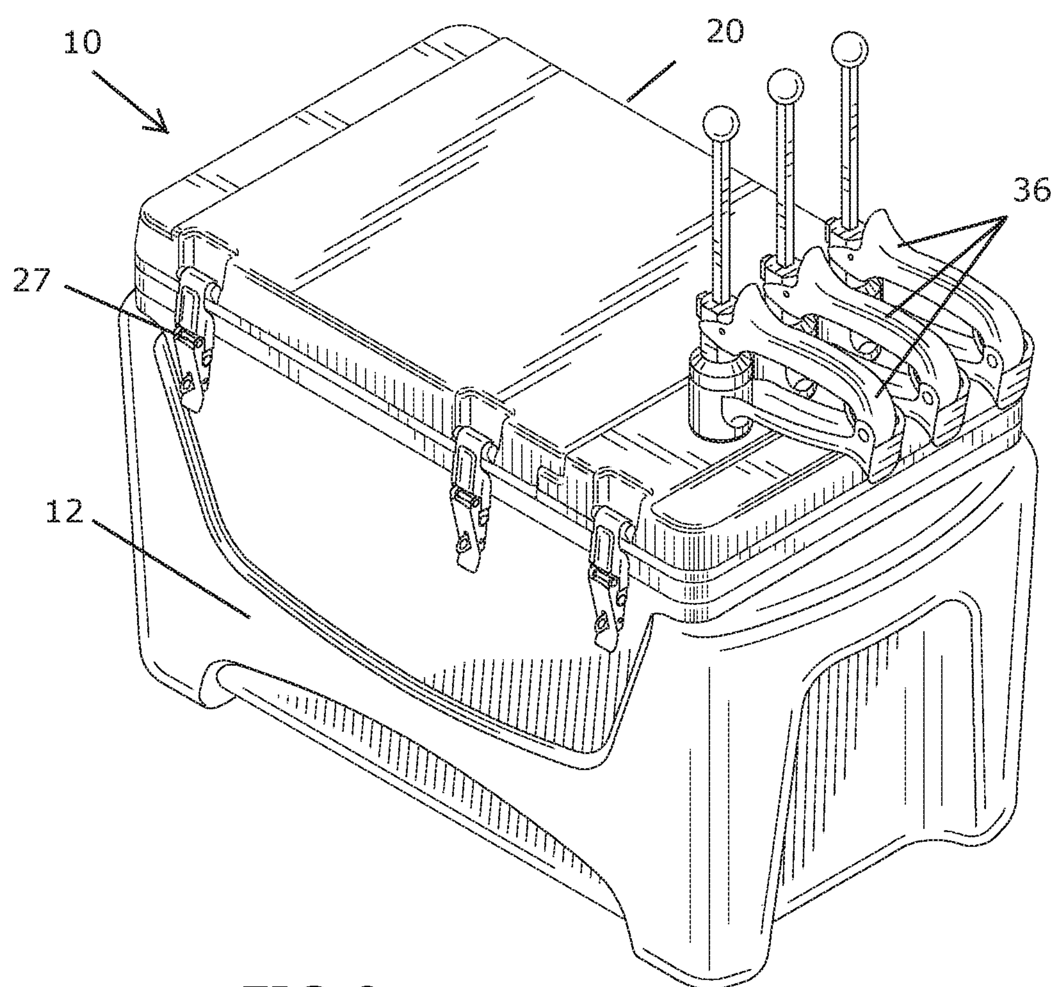
FIG. 9 is a top front perspective view of an embodiment of a livestock vaccination cooler holding a livestock medication dispenser.
Figure 10:
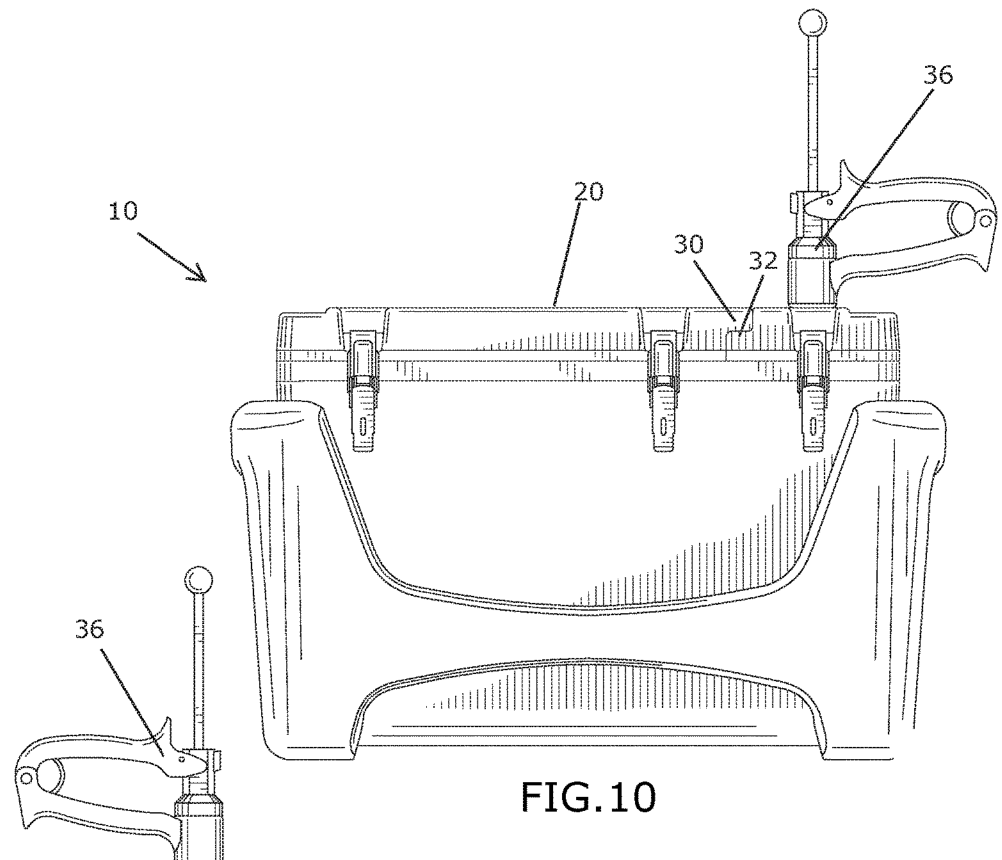
FIG. 10 is a front elevation view of the livestock vaccination cooler holding a livestock medication dispenser.
Figure 11:
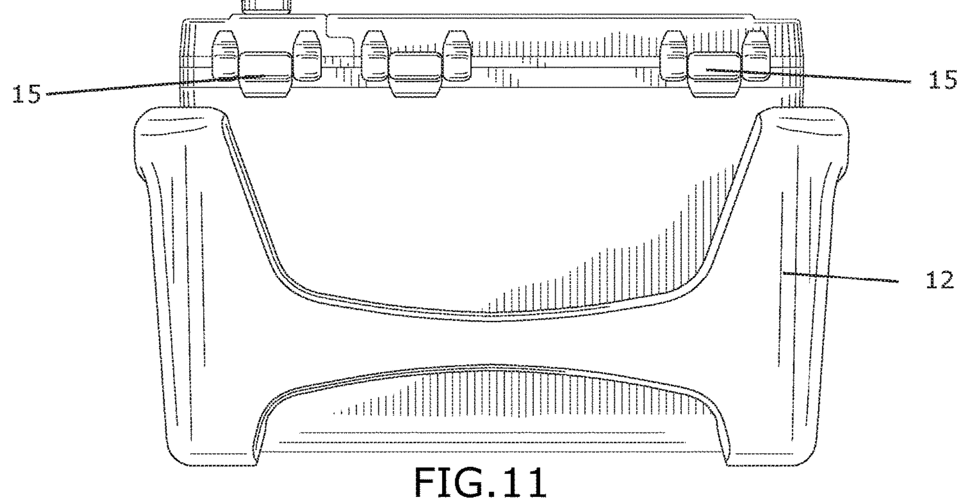
FIG. 11 is a rear elevation view of the livestock vaccination cooler holding a livestock medication dispenser.
Figure 12:
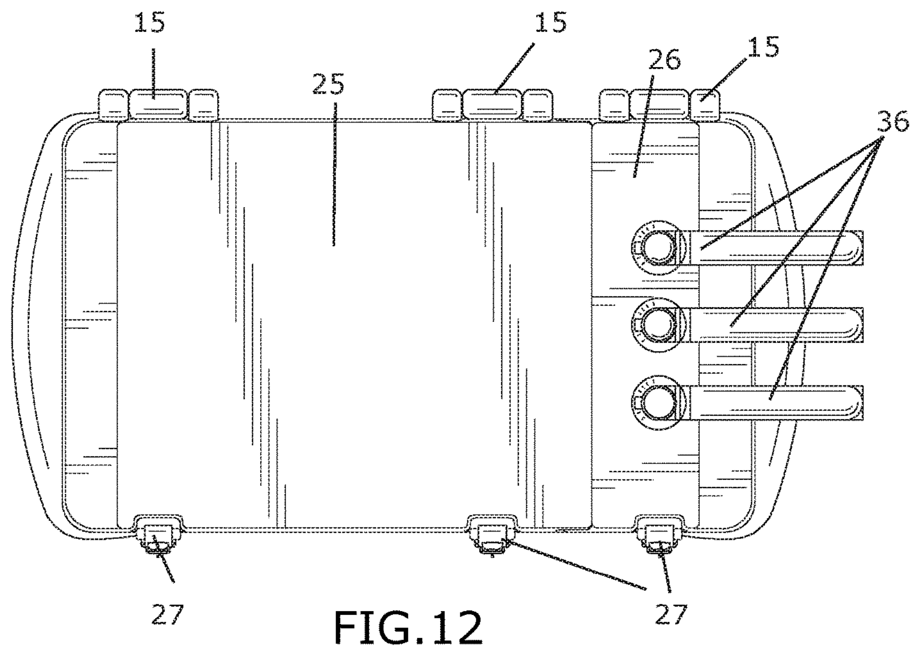
FIG. 12 is a top plan view of the livestock vaccination cooler holding a livestock medication dispenser.
Figure 13:
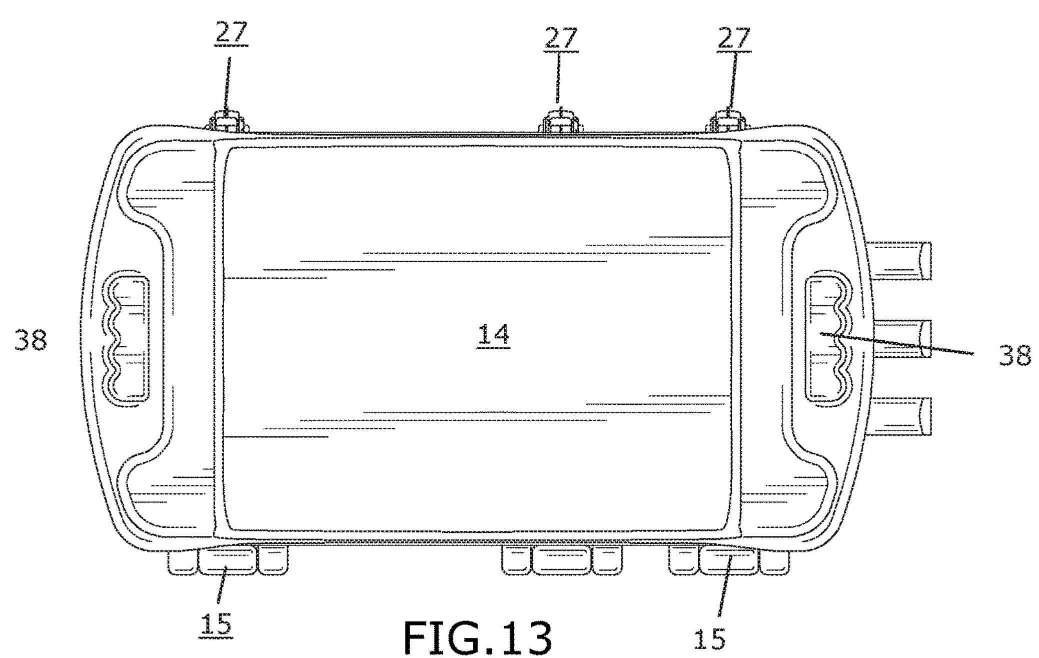
FIG. 13 is a bottom plan view of the livestock vaccination cooler holding a shown livestock medication dispenser.
Figure 14:
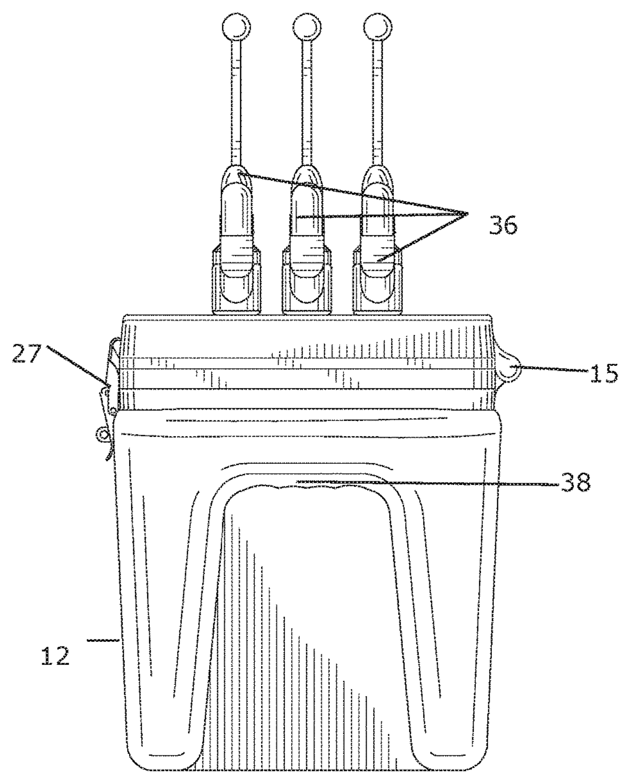
FIG. 14 is a right side elevation view of the livestock vaccination cooler holding a livestock medication dispenser.
Figure 15:
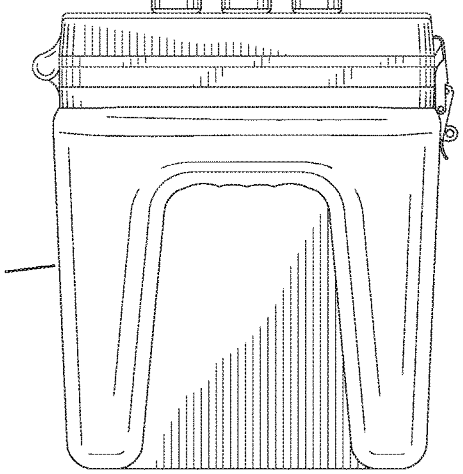
FIG. 15 is a left side elevation view of the livestock vaccination cooler shown holding a livestock medication dispenser.
Figure 16:
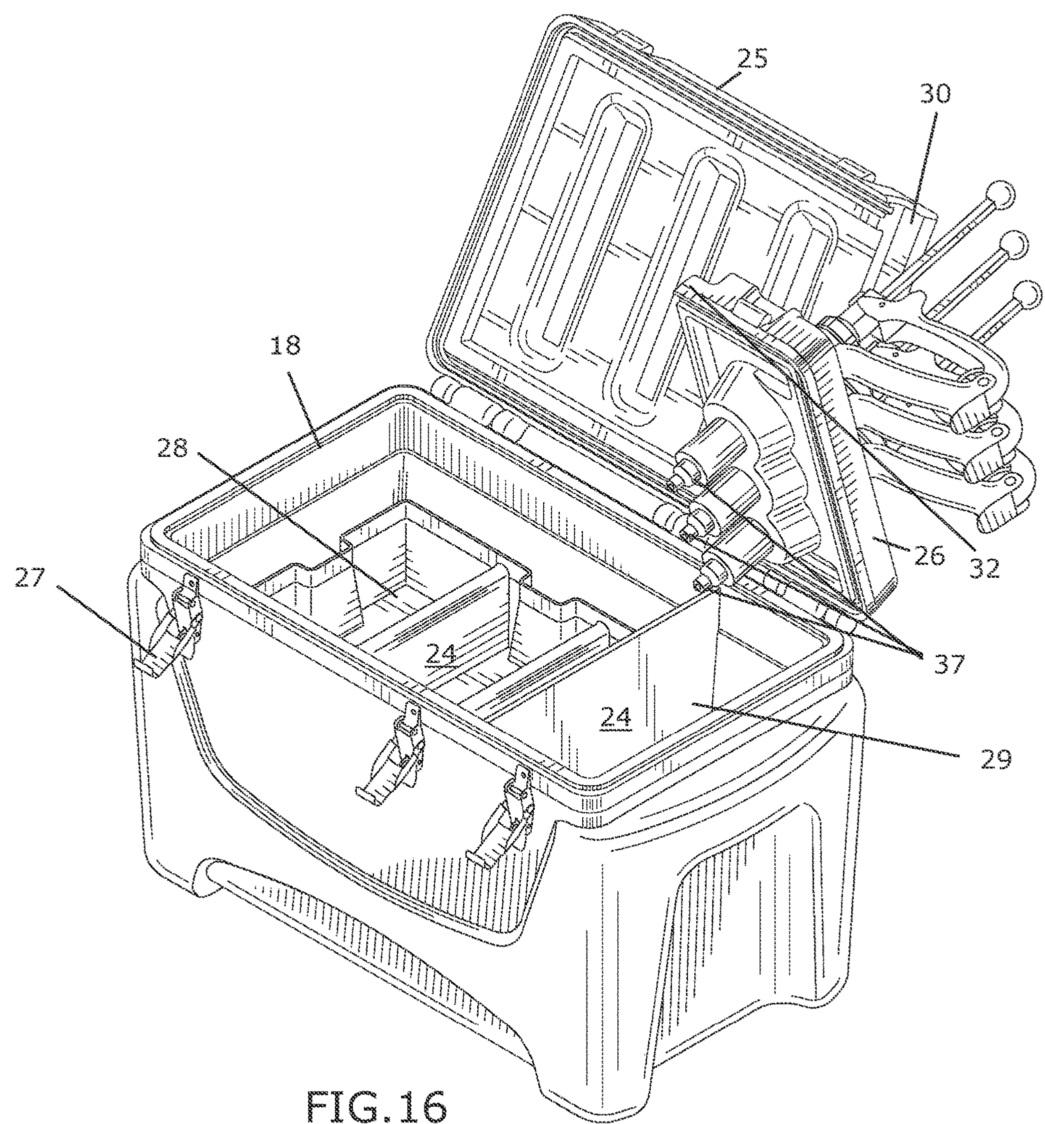
FIG. 16 is a top front perspective view of an embodiment of a livestock vaccination cooler in an open condition shown holding a livestock medication dispenser.

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Broadly, an embodiment of the present invention provides an improved livestock medication container having one or more apertures in a top lid of the container that are configured to receive a dispensing end of a livestock medication dispenser. The livestock medication dispenser 36 may include any type of medication delivery tip, including a subcutaneous injection needle, an oral administration tube, a topical applicator, a spray tip applicator, and the like that is carried on a delivery end of the livestock medication dispenser.

The livestock medication container 10 is formed by a thermally insulated body having a plurality of upstanding sidewalls 12 and a bottom wall 14 interconnecting the plurality of upstanding sidewalls 12 to define an interior cavity 16 and a top opening 18.

A top lid 20 may be movably attached to at least one of the plurality of upstanding sidewalls 12 and is movable between an open position and a closed position, such as by a hinge 15. The top lid 20 is configured to sealingly close the top opening 18 of the container when the top lid 20 is a closed position. One or more apertures 22 extend through the top lid 20. The one or more apertures 22 are configured to receive a dispensing end of a livestock medication dispenser 36 such that the delivery tip 37 may be received within an interior cavity 16 of the container 10. The sidewalls 12 may have lateral extensions for a handle 38, or handhold portion for carrying of the container.

The top lid 20 may include a first lid portion 24 covering a first portion of the top opening 18 and a second lid portion 26 covering a second portion of the top opening 18. The split top configuration permits one person to be mixing livestock medications while the another person may utilize the medication dispenser to administer one or more medications to the livestock. The top lid 20 may also include one or more latching devices 27 extending between the top lid 20 and at least one of the sidewalls 12. The one or more latching devices 27 are operable to secure the top lid 20 in the closed position.

One or more dividers 24 are removably received within the interior cavity 16 and define a plurality of compartments 28 within the thermally insulated body. The dividers 24 may include one or more panels that cooperatively engage with a channel defined in a surface of the interior cavity 16. The one or more dividers 24 may also include a bin, a tray or other receptacle. At least one of the plurality of compartments 28 are configured to receive a livestock medication vial or other medication packaging. Additional medication administration supplies, such as gloves, antiseptics, cleansing agents, record logs, writing implements may also be carried in the plurality of compartments 28. The segregation of medications provided by the compartments 28 reduces the chance of a medication being contaminated/cross contaminated, while keeping the needles and other medication administration supplies conveniently located.

Typically the livestock medication should be maintained at a controlled temperature environment to avoid spoilage of the medication or ensure the deliverability of the medication. For example, during warm environmental conditions, a cold pack may be placed within one of the compartments 28 to maintain the medication vials and delivery end of the dispenser chilled to prevent spoilage of the medication. In winter conditions, a heat pack may be carried within one of the compartments 28 to prevent freezing of the medication. The cold pack may be on of a chemically reactive composition, a frozen composition, or an electrically activated device. The heat pack may be one of an exothermic reactive composition, a heated composition, or an electrically activated heating element. The aperture 22 is preferably configured to permit the delivery tip 37 and at least a portion of the delivery device 36 so that the medication within the delivery device 36 may be thermally controlled while not being actively utilized to administer the medication to the livestock.

The first lid portion 24 covers at least one of the plurality of interior compartments 26. Similarly, the second lid portion 26 covers at least one other of the plurality of interior compartments 28. A first flange 30 may extend from an interior edge the first lid portion 24 and a second flange 32 extending from an opposed interior edge of the second lid portion 26, such that the first flange and the second flange cooperatively engage one another to seal the top opening across a transverse aspect of the thermally insulated body. The first flange 30 may overly the second flange 32 to prevent opening of the second lid portion 26 without opening the first lid portion 24. Preferably, the apertures 22 are defined in the second lid portion 26.

A containment bin 29 may be positioned within the interior cavity 16 beneath the one or more apertures 22 to capture any dripping of the medication from the dispenser 36. The containment bin 29 also serves to segregate any medication vials and other supplies from the interior cavity 16 beneath the apertures 22 to ensure that the tip 37 of the medication dispenser 36 is not damaged when the dispenser is inserted into the apertures.

It should be understood, of course, that the foregoing relates to exemplary embodiments of the invention and that modifications may be made without departing from the spirit and scope of the invention as set forth in the following claims.

What is claimed is:

1. A livestock medication container, comprising:

a thermally insulated body having a plurality of upstanding sidewalls, a bottom wall interconnecting the plurality of upstanding sidewalls to define an interior cavity, and a top opening;

a lid movably attached to at least one of the plurality of upstanding sidewalls, the lid configured to provide a closure of the top opening when placed in a closed position;

and one or more sleeves forming apertures extending through the lid, wherein the one or more sleeves extend from an interior of the lid and are dimensioned to holster a dispensing end of a livestock medication delivery device in an upright orientation.

2. The livestock medication container of claim 1, further comprising:

one or more dividers removably received within the interior cavity, to define a plurality of interior compartments.

3. The livestock medication container of claim 2, wherein the top lid further comprises:

a first lid portion covering a first portion of the top opening; and a second lid portion covering a second portion of the top opening.

4. The livestock medication container of claim 3, wherein the first lid portion covers at least one of the plurality of interior compartments.

5. The livestock medication container of claim 3, wherein the second lid portion covers another of the plurality of interior compartments.

6. The livestock medication container of claim 3, further comprising:

a first flange extending from an interior edge of the first lid portion; and a second flange extending from an interior edge of the second lid portion, wherein the first flange and the second flange cooperatively engage one another to seal the top opening across a transverse aspect of the thermally insulated body.

7. The livestock medication container of claim 6, wherein the first flange overlies the second flange preventing opening of the second lid portion without opening the first lid portion.

8. The livestock medication container of claim 3, wherein the apertures are defined in the second lid portion.

9. The livestock medication container of claim 5, wherein at least one of the plurality of interior compartments is configured to receive a livestock medication vial.

10. The livestock medication container of claim 5, wherein at least one of the plurality of interior compartments is configured to receive a thermally active package.

11. The livestock medication container of claim 10, wherein the thermally active package is a cold pack.

12. The livestock medication container of claim 10, wherein the thermally active package is a heat pack.

13. The livestock medication container of claim 1, further comprising:

a containment bin within the interior cavity positioned beneath the one or more apertures.

14. The livestock medication container of claim 1, wherein the one or more apertures are substantially cylindrical.

15. A livestock medication container, comprising: a thermally insulated body having a plurality of upstanding sidewalls, a bottom wall interconnecting the plurality of upstanding sidewalls to define an interior cavity, and a top opening;

a first lid segment and a second lid segment configured to provide a closure of a first end and a second end of the top opening when placed in a closed position, each of the first lid segment and the second lid segment movably attached to at least one of the plurality of upstanding sidewalls; and one or more sleeves forming apertures extending through the second lid segment, wherein the one or more sleeves extend from an interior of the lid and are dimensioned to retain a dispensing end of a livestock medication delivery device in an upright orientation with a delivery tip of the livestock medication device received within the interior cavity.

16. The livestock medication container of claim 15, wherein the second lid comprises at least three apertures.

17. The livestock medication container of claim 15, further comprising:

one or more dividers removably received within the interior cavity defining a plurality of interior compartments, wherein at least one of the plurality of interior compartments is a livestock medication containment bin.

18. The livestock medication container of claim 17, wherein at least one of the plurality of interior compartments is an isolation bin defined beneath the second lid portion to segregate the dispensing ends of the livestock medication delivery device from the other interior compartments.

* * * * *